US006409863B1

(12) United States Patent
Williams et al.

(10) Patent No.: US 6,409,863 B1
(45) Date of Patent: Jun. 25, 2002

(54) METHODS OF FABRICATING A CATHETER SHAFT HAVING ONE OR MORE GUIDEWIRE PORTS

(75) Inventors: Brett A. Williams, Lino Lakes; Katherine M. Prindle, Robbinsdale; Timothy M. Stivland, Plymouth, all of MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 181 days.

(21) Appl. No.: 09/591,753

(22) Filed: Jun. 12, 2000

(51) Int. Cl.⁷ .................. A61M 25/10; A61M 25/16
(52) U.S. Cl. .................. 156/198; 156/211; 156/257; 156/272.8; 156/294; 604/102.01; 604/523; 604/527; 606/194
(58) Field of Search .................. 604/96.01, 102.01, 604/102.02, 102.03, 523, 524, 527; 606/191, 194, 198; 156/198, 211, 256, 257, 272.8, 293, 294, 308.2

(56) References Cited

U.S. PATENT DOCUMENTS

| 4,093,484 A | 6/1978 | Harrison et al. | |
| 4,748,982 A | 6/1988 | Horzewski et al. | 128/344 |
| 4,762,129 A | 8/1988 | Bonzel | 128/344 |
| 4,771,777 A | 9/1988 | Horzewski et al. | 128/344 |
| 4,917,103 A | 4/1990 | Gambale et al. | 128/772 |
| 4,922,923 A | 5/1990 | Gambale et al. | 128/772 |
| 4,988,356 A | 1/1991 | Crittenden et al. | 606/192 |
| B14,762,129 A | 7/1991 | Bonzel | 606/194 |
| 5,040,548 A | 8/1991 | Yock | 128/898 |
| 5,061,273 A | 10/1991 | Yock | 606/194 |
| 5,154,725 A | 10/1992 | Leopold | 606/194 |
| 5,156,594 A | 10/1992 | Keith | 604/96 |
| 5,171,222 A * | 12/1992 | Euteneuer et al. | 604/103.1 |
| 5,180,367 A | 1/1993 | Kontos et al. | 604/101 |
| 5,217,482 A | 6/1993 | Keith | 606/194 |
| 5,232,445 A | 8/1993 | Bonzel | 604/96 |
| 5,267,958 A | 12/1993 | Buhbinder et al. | |
| 5,279,562 A | 1/1994 | Sirhan et al. | 604/96 |
| 5,300,025 A | 4/1994 | Wantink | 604/96 |
| 5,300,085 A | 4/1994 | Yock | 606/191 |
| 5,306,247 A | 4/1994 | Pfenninger | 604/96 |
| 5,324,269 A | 6/1994 | Miraki | 604/160 |
| 5,350,395 A | 9/1994 | Yock | 606/194 |
| 5,364,376 A | 11/1994 | Horzewski et al. | 604/280 |

(List continued on next page.)

FOREIGN PATENT DOCUMENTS

WO   WO 01/70323 A1   9/2001

Primary Examiner—Jeff H. Aftergut
Assistant Examiner—Barbara J. Musser
(74) Attorney, Agent, or Firm—Crompton, Seager & Tufte LLC

(57) ABSTRACT

A method of fabricating a catheter shaft having one or more guidewire ports is disclosed. A method in accordance with the present invention includes the steps of cutting the wall of a first shaft portion to create an opening defined by the wall of the first shaft portion, inserting the proximal end of an inner member through the opening defined by the wall of the first shaft portion, inserting the distal end of the inner member into the lumen of a second shaft portion, inserting the bonding end the second shaft portion into a lumen defined by first shaft portion, and bonding the bonding portion of the first shaft portion to the bonding portion of the second shaft portion.

28 Claims, 18 Drawing Sheets

U.S. PATENT DOCUMENTS

| | | | |
|---|---|---|---|
| 5,370,616 A | 12/1994 | Keith et al. | 604/102 |
| 5,389,087 A | 2/1995 | Miraki | 604/247 |
| 5,395,334 A | 3/1995 | Keith et al. | 604/102 |
| 5,410,797 A | 5/1995 | Steinke et al. | 29/435 |
| 5,425,711 A | 6/1995 | Resssemann et al. | 604/96 |
| 5,451,233 A | 9/1995 | Yock | 606/194 |
| 5,458,613 A | 10/1995 | Gharibadeh et al. | 606/194 |
| 5,490,837 A | 2/1996 | Blaeser et al. | 604/96 |
| 5,496,346 A | 3/1996 | Horzewski et al. | 606/194 |
| 5,522,818 A | 6/1996 | Keith et al. | 604/102 |
| 5,531,690 A | 7/1996 | Solar | 604/102 |
| 5,626,600 A | 5/1997 | Horzewski et al. | 606/194 |
| 5,637,902 A | 6/1997 | Jiang | 257/379 |
| 5,658,251 A | 8/1997 | Ressemann et al. | 604/102 |
| 5,702,439 A * | 12/1997 | Keith et al. | 604/524 |
| 5,709,658 A | 1/1998 | Sirhan et al. | 604/102 |
| 5,718,683 A | 2/1998 | Ressemann et al. | 604/96 |
| 5,749,888 A | 5/1998 | Yock | 606/194 |
| 5,769,868 A | 6/1998 | Yock | 606/194 |
| 5,810,869 A | 9/1998 | Kaplan et al. | 606/194 |
| 5,833,706 A | 11/1998 | St. Germain et al. | 606/194 |
| 5,921,971 A | 7/1999 | Agro et al. | 604/280 |
| 5,961,485 A | 10/1999 | Martin | |
| 5,961,490 A | 10/1999 | Adams | 604/96 |
| 5,980,484 A | 11/1999 | Ressemann et al. | 604/96 |
| 5,980,486 A | 11/1999 | Enger | 604/102 |
| 6,027,475 A | 2/2000 | Sirhan et al. | 604/96 |
| 6,030,405 A | 2/2000 | Zarbatany et al. | 606/191 |
| 6,036,715 A | 3/2000 | Yock | 606/194 |
| 6,048,338 A | 4/2000 | Larson et al. | 604/523 |
| 6,059,748 A | 5/2000 | Teirstein et al. | 604/53 |
| 6,066,114 A | 5/2000 | Goodin et al. | 604/102 |
| 6,102,890 A | 8/2000 | Stivland et al. | 604/96 |
| 6,129,708 A | 10/2000 | Enger | 604/103.04 |
| 6,190,358 B1 * | 2/2001 | Fitzmaurice et al. | 604/102.02 |

\* cited by examiner

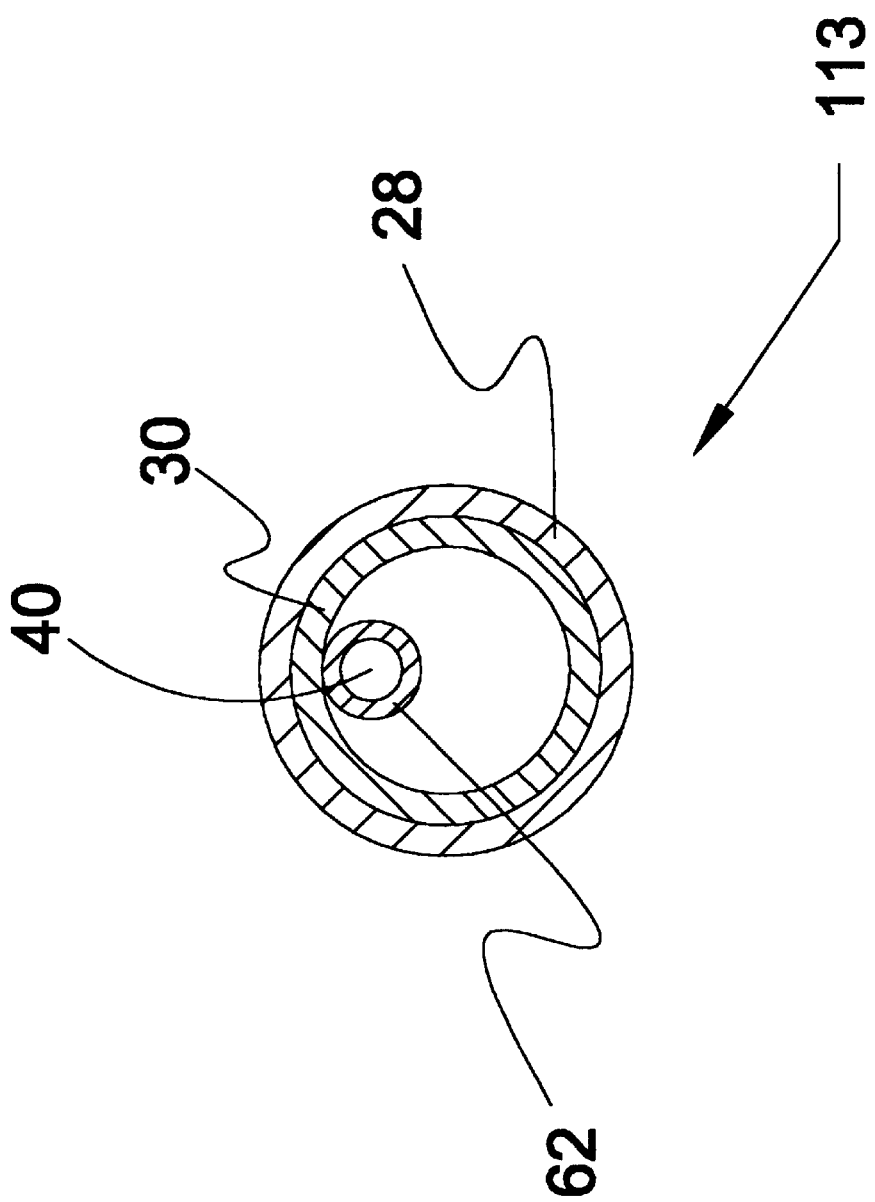

METHODS OF FABRICATING A CATHETER SHAFT HAVING ONE OR MORE GUIDEWIRE PORTS

FIELD OF THE INVENTION

The present invention relates generally to catheters for performing medical procedures. More particularly, the present invention relates to methods of fabricating catheter shafts having one or more guidewire ports and two or more tubular members.

BACKGROUND OF THE INVENTION

Intravascular catheters are currently utilized in a wide variety of minimally-invasive medical procedures. Generally, an intravascular catheter enables a physician to remotely perform a medical procedure by inserting the catheter into the vascular system of the patient at a location that is easily accessible and thereafter navigating the catheter to the desired target site. By this method, virtually any target site in the patient's vascular system may be remotely accessed, including the coronary, cerebral, and peripheral vasculature.

Typically, the catheter enters the patient's vasculature at a convenient location such as a blood vessel in the neck or near the groin. Once the distal portion of the catheter has entered the patient's vascular system the physician may urge the distal tip forward by applying longitudinal forces to the proximal portion of the catheter. For the catheter to effectively communicate these longitudinal forces it is desirable that the catheter have a high level of pushability and kink resistance.

Frequently the path taken by a catheter through the vascular system is tortuous, requiring the catheter to change direction frequently. In some cases, it may even be necessary for the catheter to double back on itself. In order for the catheter to conform to a patient's tortuous vascular system, it is desirable that intravascular catheters be very flexible, particularly in the distal portion.

While advancing the catheter through the tortuous path of the patients vasculature, physicians often apply torsional forces to the proximal portion of the catheter to aid in steering the catheter. To facilitate the steering process, the distal portion of the catheter may include a plurality of bends or curves. Torsional forces applied on the proximal end must translate to the distal end to aid in steering. It is therefore desirable that an intravascular catheter have a relatively high level of torquability to facilitate steering.

After the intravascular catheter has been navigated through the patient's vascular system so that its distal end is adjacent the target site, the catheter may be used for various diagnostic and/or therapeutic purposes. One example of a diagnostic use for an intravascular catheter is the delivery of radiopaque contrast solution to enhance fluoroscopic visualization. In this application, the intravascular catheter provides a fluid path leading from a location outside the body to a desired location inside the body of a patient. In order to maintain a fluid path, it is desirable that the intravascular catheter be sufficiently resistant to kinking. In addition, because such fluids are delivered under pressure, it is desirable that the intravascular catheter be sufficiently resistant to bursting or leaking.

Examples of therapeutic purposes for intravascular catheters include percutaneous transluminal angioplasty (PTA) and percutaneous transluminal coronary angioplasty (PTCA). These angioplasty techniques typically involve the use of a guide catheter and a balloon catheter. During these procedures, the distal end of the guide catheter is typically inserted into the femoral artery located near the groin of the patient. The guide catheter is urged through the vasculature of the patient until its distal end is proximate the restriction. In many cases, the distal end of the guide catheter is positioned in the ostium of the coronary artery. The balloon catheter may then be fed through a lumen in the guide catheter such that the balloon is positioned proximate a restriction in a diseased vessel. The balloon is then inflated and the restriction in the vessel is opened. In this application, it is desirable that the guide catheter provide a low friction path for the balloon catheter. The balloon is inflated by urging a liquid though the elongate shaft of the balloon catheter and into the balloon. In this application, the balloon catheter must provide an unobstructed path for the inflation fluid. It is also desirable that the catheter be substantially free of leaks.

As described at length above, it is desirable to combine a number of performance features in an intravascular catheter. It is desirable that the catheter have a relatively high level of pushability and torqueability. It is also desirable that a catheter be relatively flexible, particularly near it's distal end. The need for this combination of performance features is often addressed by building a catheter which has two or more discrete tubular members having different performance characteristics. For example, a relatively flexible distal section may be spliced to a relatively rigid proximal section. When a catheter is formed from two or more discrete tubular members, it is necessary to form a bond between the distal end of one tubular member and the proximal end of another tubular member.

Intravascular catheters are often used in conjunction with a guidewire. When this is the case, the guidewire may be advanced through the patient's vasculature until its distal tip has reached a desired target location. Once the distal portion of the guidewire has reached the desired location, a catheter may be threaded onto the guidewire and urged distally until the distal end of the catheter is proximate the target location.

Intravascular catheters adapted for use with guidewire typically fall into one of two categories: 1) single operator exchange (SOE); or 2) over-the-wire types. An over-the-wire type of catheter includes a guidewire lumen extending from the distal tip of the catheter to the proximal end of the catheter. Whereas, a single operator exchange catheter typically includes a relatively short guidewire lumen proximate the distal end of the catheter.

Single operator exchange catheters were developed in response to difficulties encountered when exchanging over-the-wire catheters. During a medical procedure utilizing intravascular catheters it is sometimes necessary to withdraw one catheter and replace it with a second catheter. Generally the catheter is withdrawn from the patient over the guidewire leaving the guidewire in place with the distal tip of the guidewire proximate the target location of the patient's anatomy.

In order to withdraw the catheter while leaving the guidewire in the desired location, a portion of the guidewire is typically grasped by the physician in order to hold the guidewire in place. During this procedure, a portion of the guidewire must be exposed at all times so that it is available for the physician to grasp. In the case of over-the-wire catheter, this requires that the length of guidewire extending beyond the patient's body be longer than the catheter. In some cases, length may be added to the guidewire using a guidewire extension. The long exchange wire or guidewire extension extending beyond the patient's body must be managed during the catheter exchange procedure. In particular, contamination must be avoided by making sure that the guidewire is not dropped from the sterile field. This procedure is awkward and typically requires two persons.

An SOE catheter, on the other hand, has a relatively short guidewire lumen. The length of guidewire extending from the patient need only be slightly longer than the guidewire lumen of the catheter. The physician may anchor or hold the guidewire as the catheter is removed from the body with the exchange occurring over the shorter guidewire lumen. The guidewire lumen of an SOE catheter typically includes a distal guidewire port disposed at the distal tip of the catheter and a proximal guidewire port disposed proximally of the distal end of the catheter. It is desirable to fabricate SOE catheters including a proximal guidewire port while maintaining the other desirable performance features described previously.

SUMMARY OF THE INVENTION

The present invention relates generally to catheters for performing medical procedures. More particularly, the present invention relates to methods of fabricating catheters having one or more guidewire ports and two or more tubular members.

A catheter assembly in accordance with the present invention includes an elongate shaft having a proximal shaft portion, a middle shaft portion, and a distal shaft portion. Proximal shaft portion, a middle shaft portion, and a distal shaft portion each have a proximal end an a distal end. The distal end of the proximal shaft portion is fixed to the proximal end of the middle shaft portion. Likewise, the distal end of middle shaft portion is fixed to the proximal end of distal shaft portion at a transition region.

In a presently preferred embodiment the catheter includes a proximal guidewire port disposed proximate the transition region. The catheter further includes a distal guidewire port disposed proximate the distal end of the distal shaft portion. The elongate shaft of the catheter includes a plurality of walls defining a guidewire lumen which is in fluid communication with the proximal guidewire port and the distal guidewire port.

The elongate shaft also includes a plurality of walls defining an inflation lumen. The inflation lumen is in fluid communication with a balloon disposed proximate the distal end of the elongate shaft of the catheter. The inflation lumen is also in fluid communication with a port of a hub assembly disposed at the proximal end of the elongate shaft of the catheter. A fluid source may be coupled to the port of the hub assembly. The balloon may be inflated by urging fluid from the fluid source into the balloon via the inflation lumen.

The inflation lumen and the guidewire lumen both pass through the transition region of the catheter. In a presently preferred embodiment, the distal end of middle shaft portion is fixed to the proximal end of distal shaft portion proximate the transition region of the catheter. Methods of fabricating a catheter having such a transition region are disclosed.

BRIEF DESCRIPTION OF THE DRAWINGS

FIG. 17 is a transverse cross sectional view of the assembly of FIG. 16;

DETAILED DESCRIPTION OF THE INVENTION

The following detailed description should be read with reference to the drawings, in which like elements in different drawings are numbered identically. The drawings which are not necessarily to scale, depict selected embodiments and are not intended to limit the scope of the invention. Examples of constructions, materials, dimensions, and manufacturing processes are provided for various elements. Those skilled in the art will recognize that many of the examples provided have suitable alternatives which may be utilized.

Figure 1:
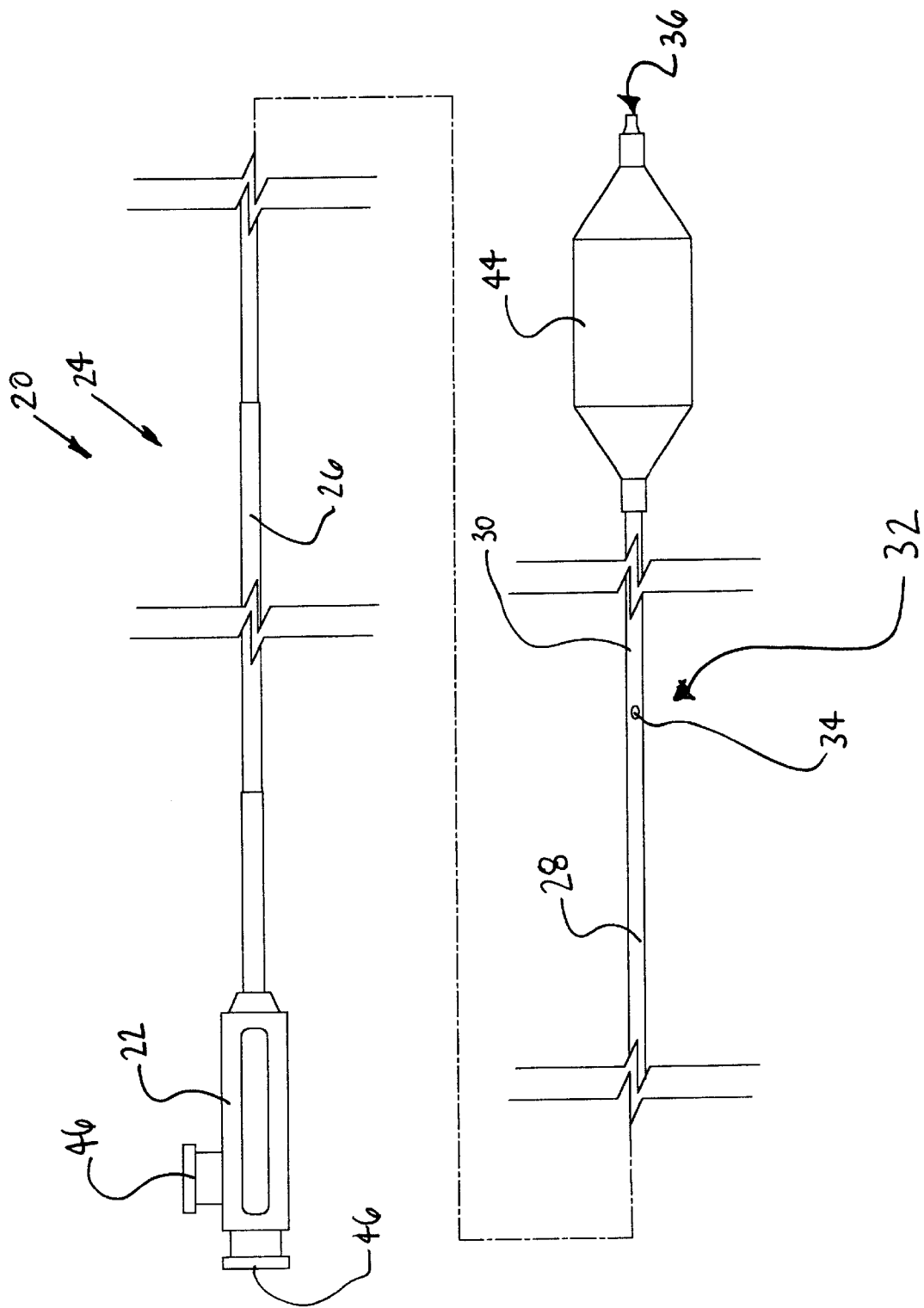
FIG. 1 is a plan view of an exemplary embodiment of a catheter in accordance with the present invention.

Refer now to FIG. 1, which illustrates a plan view of a catheter 20 in accordance with an exemplary embodiment of the present invention. Catheter 20 includes a hub 22 connected to the proximal end of an elongate shaft 24.

Elongate shaft 24 includes a proximal shaft portion 26, a middle shaft portion 28, and a distal shaft portion 30. Proximal shaft portion 26, a middle shaft portion 28, and a distal shaft portion 30 each having a proximal end and a distal end. As shown in FIG. 1, the distal end of proximal shaft portion 26 is fixed to the proximal end of middle shaft portion 28. Likewise, the distal end of middle shaft portion 28 is fixed to the proximal end of distal shaft portion at a transition region 32. Those of skill in the art will appreciate that catheter 20 may include more or less than three shaft portions without deviating from the spirit and scope of the present invention.

In the embodiment of FIG. 1, catheter 20 includes a proximal guidewire port 34 disposed proximate transition region 32. Catheter 20 also includes a distal guidewire port 36 disposed proximate the distal end of distal shaft portion 30. Elongate shaft 24 includes a plurality of walls 38 defining a guidewire lumen 40 which is in fluid communication with proximal guidewire port 34 and distal guidewire port 36.

Elongate shaft 24 also includes a plurality of walls defining an inflation lumen 42. Inflation lumen 42 is in fluid communication with a balloon 44 and a port 46 of hub 22. A fluid source 48 (not shown) may be coupled to a port 46 of hub 22. Balloon 44 may be inflated by urging fluid from fluid source 48 into balloon 44 via inflation lumen 42. Catheter 20 of FIG. 1 is a type of catheter which may be generally referred to as a balloon catheter. Those of skill in the art will appreciate that methods and devices in accordance with the present invention may be used to fabricate other types of catheter.

Figure 2:
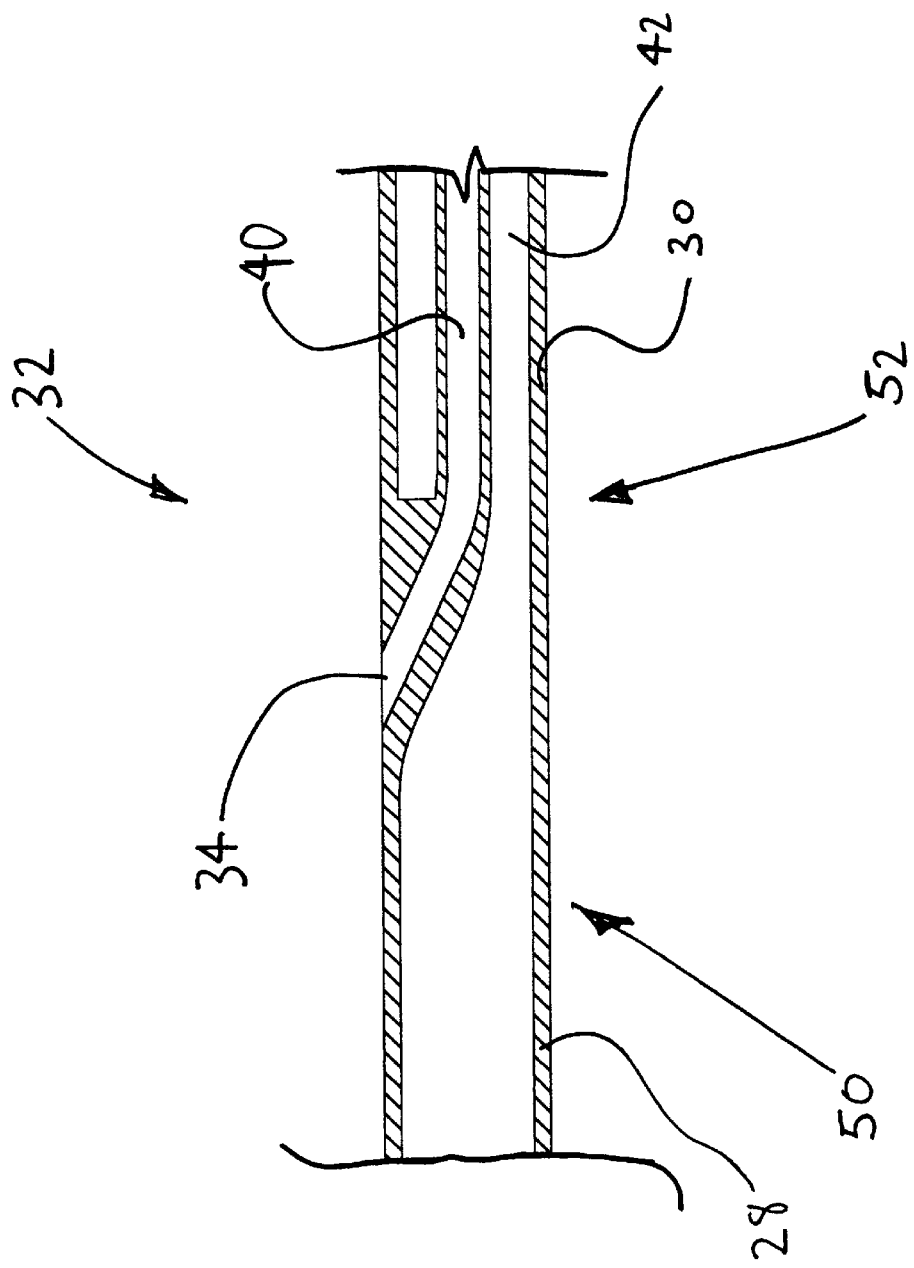
FIG. 2 is a cross-sectional view of the transition region 32 of an exemplary embodiment of a catheter in accordance with the present invention.

FIG. 2 is a cross-sectional view of transition region 32 of catheter 20. As shown in FIG. 2, distal portion 50 of middle shaft portion 28 has been bonded to proximal portion 52 of distal shaft portion 30. Guidewire lumen 40 extends between proximal guidewire port 34 and distal guidewire port 36 (not shown). Inflation lumen 42 extends through transition region 32.

Figure 3:
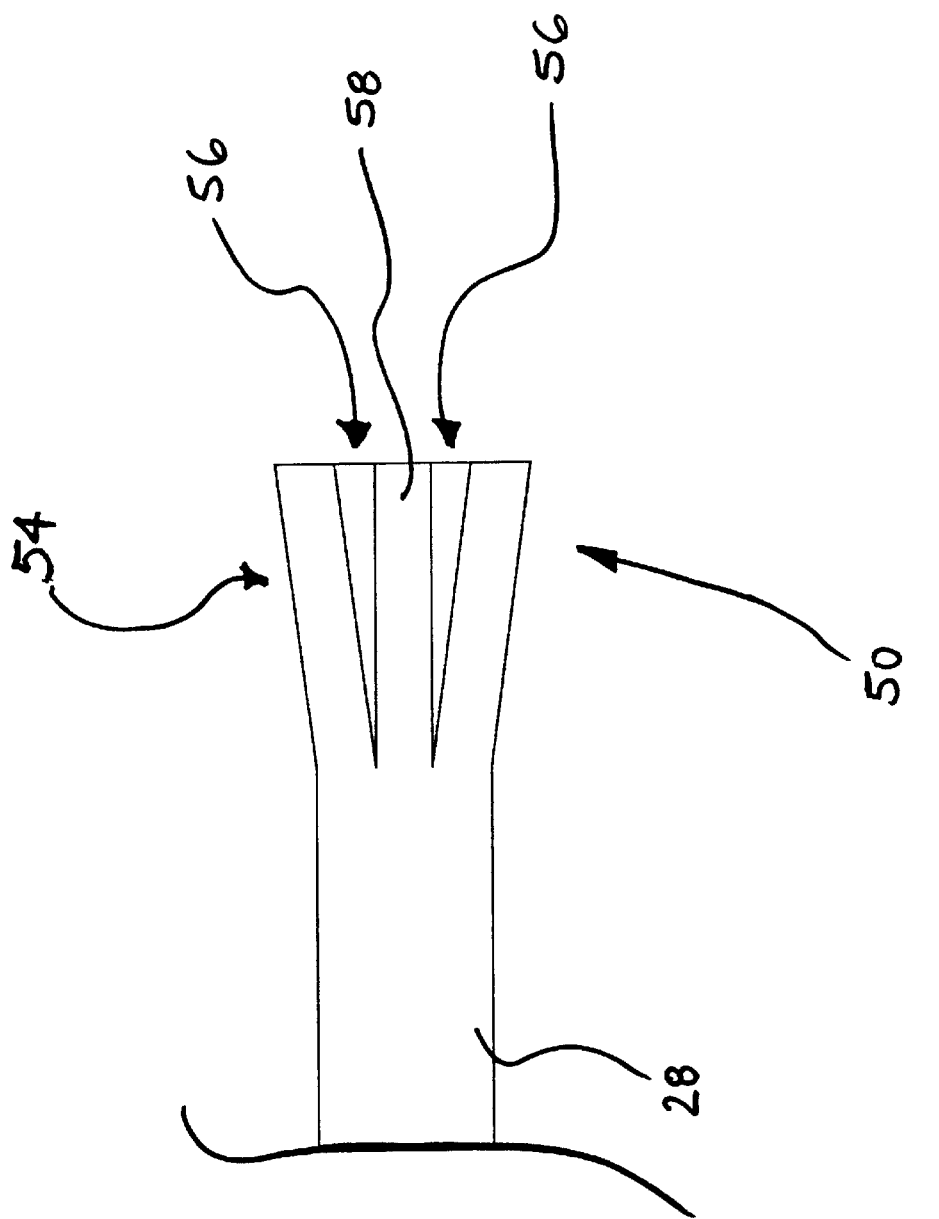
FIG. 3 is a plan view of the distal portion of an generally tubular member in accordance with the an exemplary embodiment of the present invention.

FIGS. 3–7 may be utilized to describe one method which may be used to fabricate transition region 32 of catheter 20. FIG. 3 is a plan view of distal portion 50 of middle shaft portion 28 prior to joining. In FIG. 3, middle shaft portion 28 has an enlarged portion 54 proximate its distal portion 50. In a presently preferred embodiment of the present invention, enlarged portion 54 of middle shaft portion 28 facilitates the insertion of proximal portion 52 of distal shaft portion 30 into the lumen defined by distal portion 50 of middle shaft portion 28. Alternate embodiments of the present invention have been envisioned in which middle shaft portion 28 does not include enlarged portion 54. In these envisioned embodiments, proximal portion 52 of distal shaft portion 30 may be press fit into distal portion 50 of middle shaft portion 28. Middle shaft portion 28 also includes a plurality of slits 56 which define a tongue 58.

Those of skill in the art will appreciate that middle shaft portion 28 may be comprised of many materials without deviating from the spirit and scope of the present invention. For example, middle shaft portion 28 may include an inner tube comprised of PTFE. By way of a second example, middle shaft portion 28 may include a support member. In a preferred embodiment, a support member is comprised of a plurality of fibers wound in a braided pattern around an inner tube. In a preferred embodiment, middle shaft portion 28 is comprised of polyether block amide (PEBA). Polyether block amide is commercially available from Atomchel Polymers of Birdsboro, Pa. under the tradename PEBAX. Middle shaft portion 28 may be fabricated using an extrusion process. In this process, molten PEBA is extruded onto the combined layers of the inner tube and the support member. When this process is used, the PEBA material fills any interstitial spaces in the support member. It is to be understood that other manufacturing processes can be used without deviating from the spirit and scope of the present invention. Middle shaft portion 28 may also be comprised of other materials without deviating from the scope or spirit of this invention. Examples of materials which may be suitable in some applications include: polyethylene (PE), polypropylene (PP), polyvinylchloride (PVC), polyurethane, and PTFE.

Figure 4:
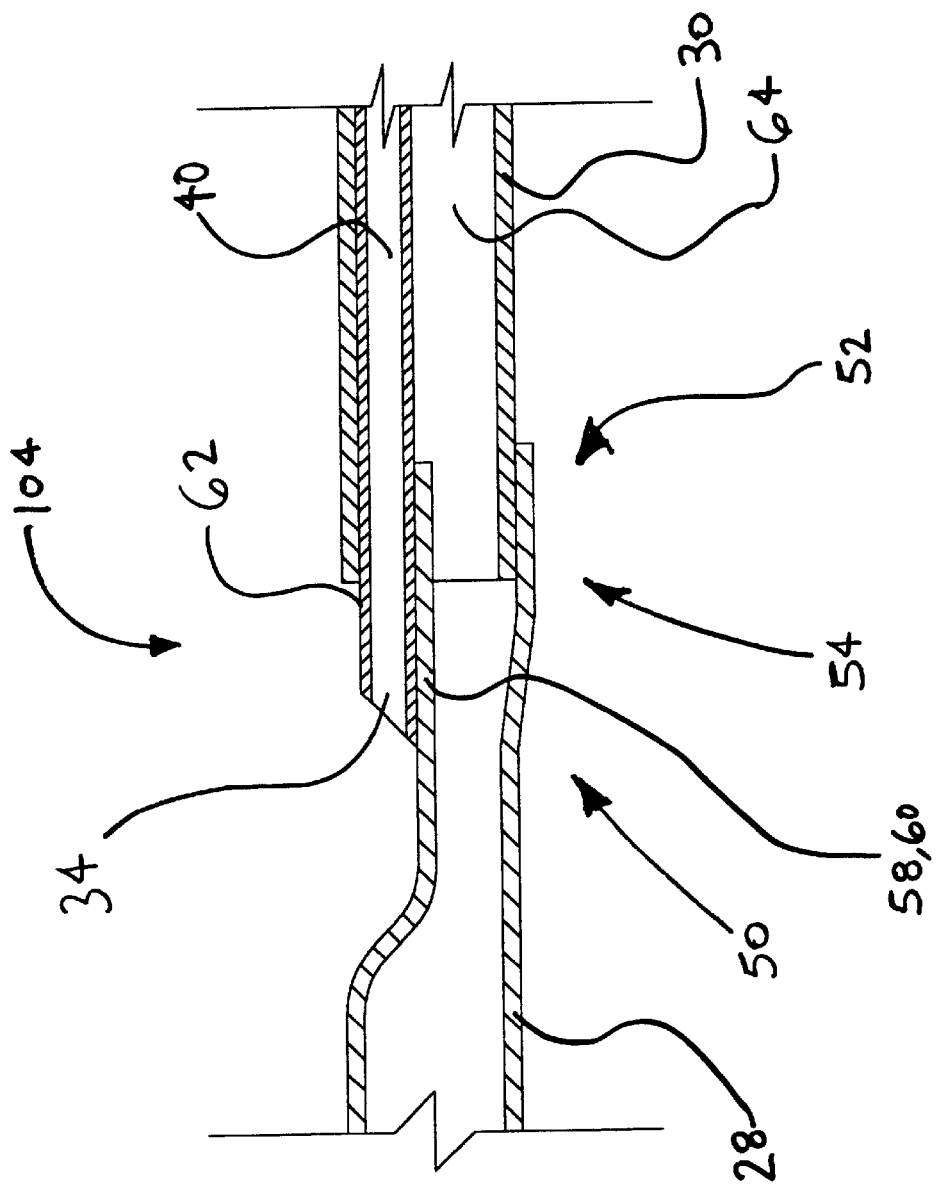
FIG. 4 is a cross sectional view of an assembly in accordance with the present invention, the assembly includes two shaft portions, and an inner tubular member.

FIG. 4 is a cross sectional view of an assembly 104 including middle shaft portion 28. In FIG. 4, tongue 58 of middle shaft portion 28 has been positioned under an inner tubular member or inner 62. When tongue 58 is positioned in this way, it forms a shelf 60. The proximal end of distal shaft portion 30 has been inserted into enlarged portion 54 of middle shaft portion 28. An inner tubular member or inner 62 is disposed proximate shelf 60 formed by tongue 58. As show in FIG. 4, a portion of inner tubular member is disposed within a distal lumen 64 defined by distal shaft portion 30. In a presently preferred embodiment, inner 62 defines proximal guidewire port 34, guidewire lumen 40 and distal guidewire port 36 (not shown).

Figure 5:
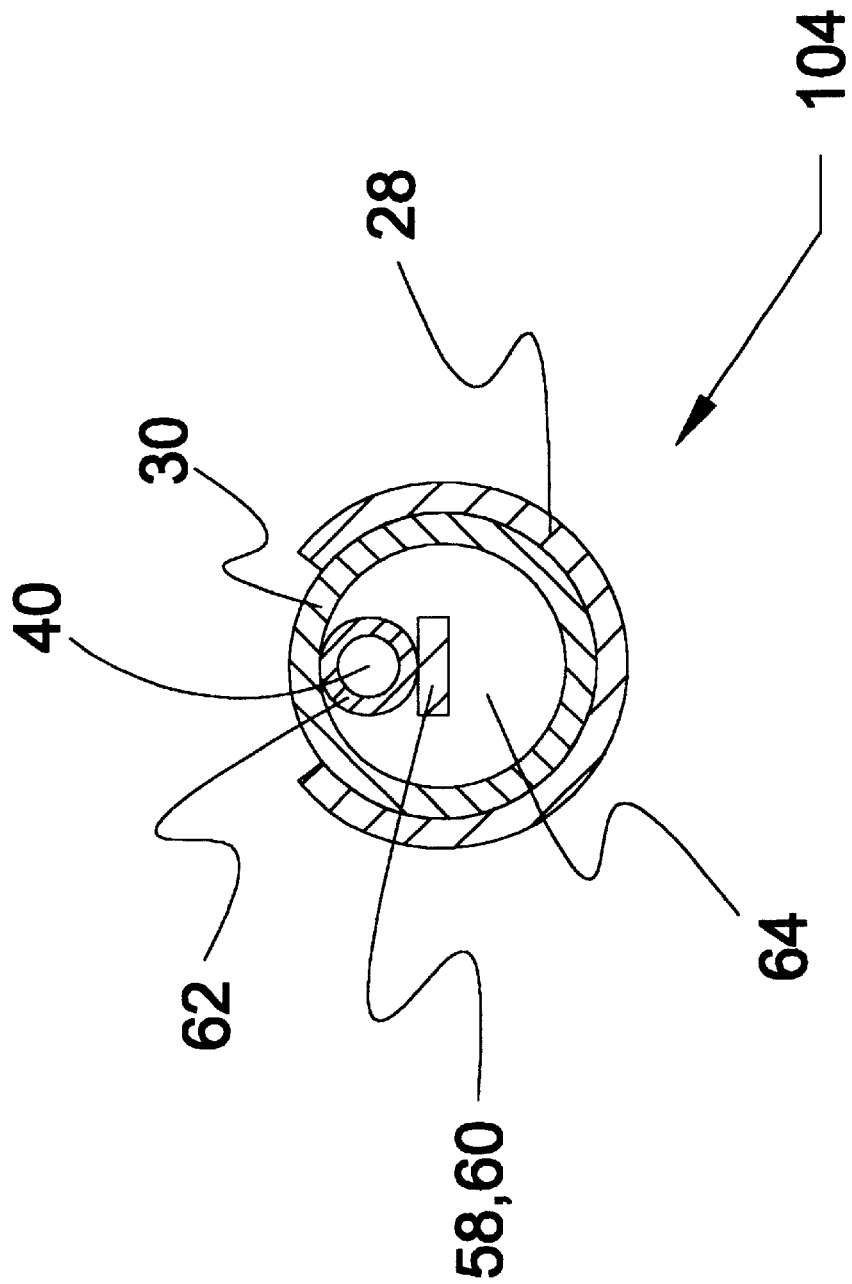
FIG. 5 is a transverse cross sectional view of the assembly of FIG. 4.

FIG. 5 is a transverse cross sectional view of assembly 104 of FIG. 4. In FIG. 5, middle shaft portion 28 is shown disposed about distal shaft portion 30. Inner 62 is shown disposed within distal lumen 64 of distal shaft portion 30, proximate shelf 60 formed by tongue 50. Guide wire lumen 40 defined by inner 62 is also shown in FIG. 5.

Figure 6:
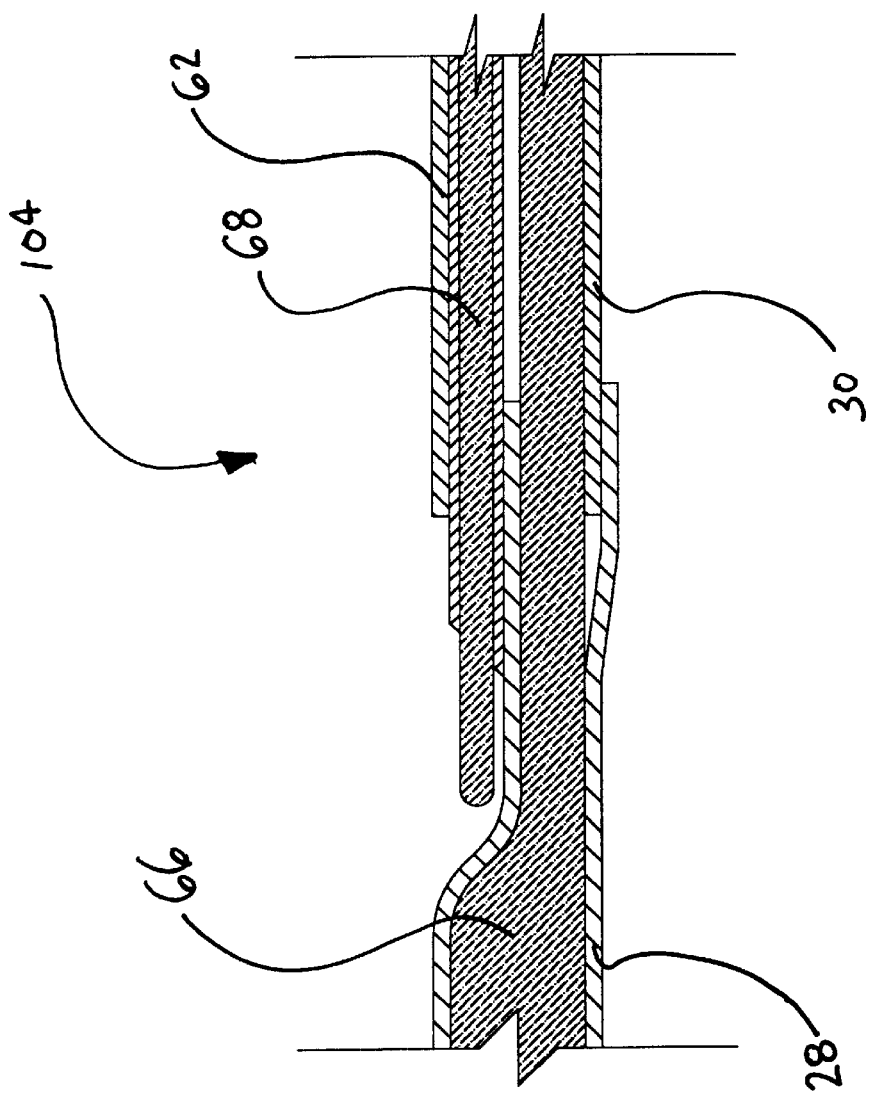
FIG. 6 is a cross sectional view of the assembly of FIG. 4 with a first mandrel disposed within the lumens of the middle shaft portion and the distal shaft portion and a second mandrel disposed within the guidewire lumen of the inner tubular member.

FIG. 6 is a cross sectional view of assembly 104 of FIG. 4 and FIG. 5 with a first mandrel 66 disposed within the lumens of middle shaft portion 28 and distal shaft portion 30. In FIG. 6 a second mandrel 68 is disposed within guidewire lumen 40 of inner 62.

Figure 7:
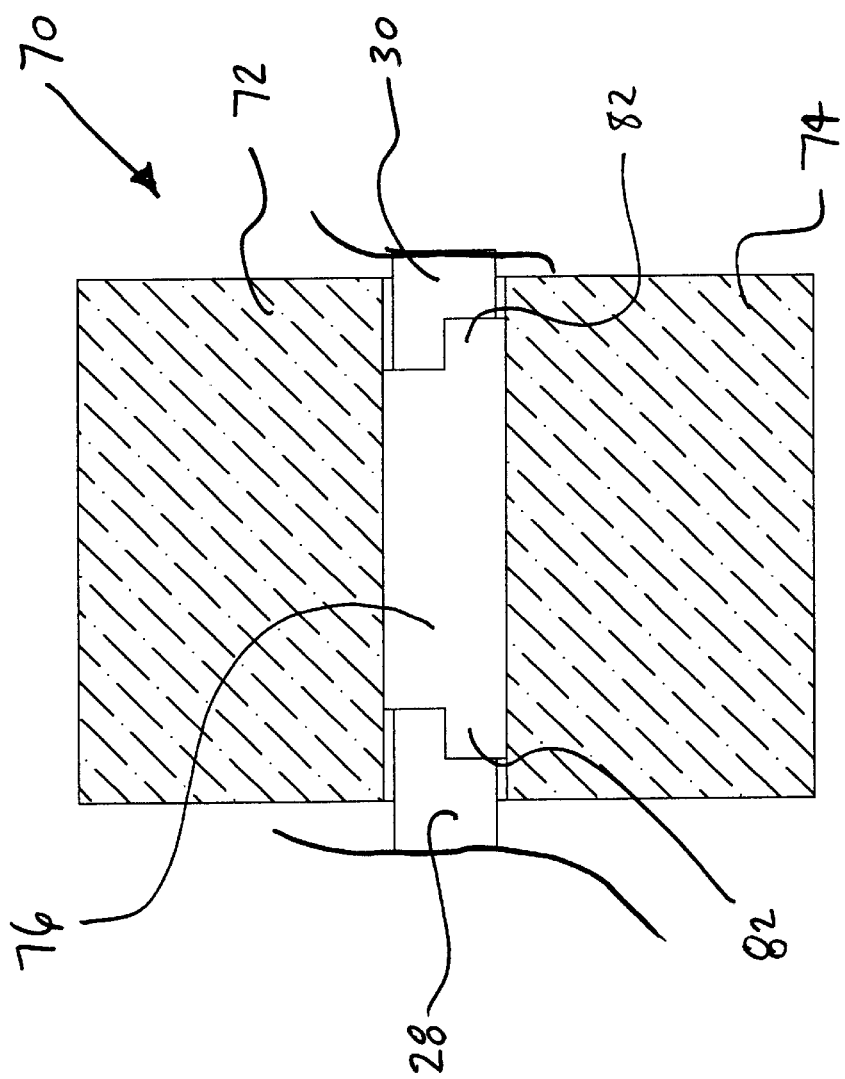
FIG. 7 is a cross sectional view of a compression fixture including a first die and a second die.

FIG. 7 is a cross sectional view of a compression fixture 70 including a first die 72 and a second die 74. A sleeve 76 is disposed about assembly 104 of FIG. 6. Middle shaft portion 28 and distal shaft portion 30 are shown extending beyond the ends of sleeve 76. Sleeve 76 and assembly 104 are disposed between first die 72 and second die 74 of compression fixture 70.

In the embodiment of FIG. 7, sleeve 76 includes a plurality of ears 82. In a preferred embodiment, sleeve 76 is comprised of PTFE heat shrink tubing. In another embodiment, polyolefin heat shrink can be used. Suitable PTFE and polyolefin heat shrink tubing is commercially available from Zeus Industries of Orangeburg, S.C. and Raychem Corporation of Menlo Park, Calif. Those of skill in the art will appreciate that sleeve 76 may be comprised of materials other than PTFE shrink tubing without deviating from the spirit and scope of the present invention. Sleeve 76 need not necessarily be comprised of shrink tubing and sleeve 76 need not be comprised of PTFE.

Figure 8:
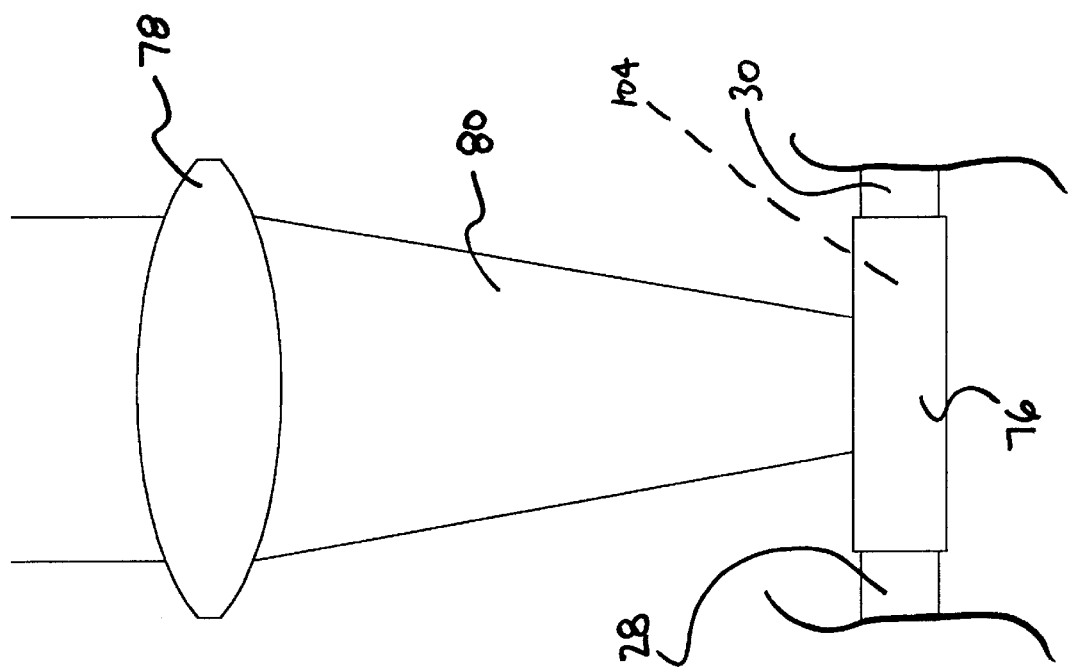
FIG. 8 is a plan view illustrating a method which may be used to fuse the transition portion of a catheter.

FIG. 8 is a plan view of a lens 78 capable of focusing a laser beam 80. In FIG. 8, laser beam 80 is illuminating a portion of assembly 104 and sleeve 76. A method of fabricating transition region 32 of catheter 20 may be described with reference to FIGS. 3–7.

A presently preferred method in accordance with the present invention begins with the step of forming enlarged portion 54 proximate the distal end of middle shaft portion 28. This may be accomplished using a heat forming process. A suitable heat forming process typically includes the steps of applying heat and forming the material. Forming the material may by accomplished by urging an appropriately shaped mandrel into the lumen of middle shaft portion 28.

A number of methods may be used to apply heat to the material of middle shaft portion 28 including convection, conduction and radiation. An example of heating with radiant energy is directing infrared energy from an infrared heat source at the material. Infrared energy sources suitable for this process are commercially available from Research Incorporated of Minnetonka, Minn. An example of heating with convection is directing a flow of hot air from a hot air gun so that it impinges on the material. Hot air guns suitable for this application are commercially available from Leister Elektro-Geratebau of Lucerne, Switzerland.

Enlarged portion 54 of middle shaft portion 28 may be allowed to cool. Slits 56 may be formed by cutting through the material of middle shaft portion with a cutting tool. Any suitable cutting tool may be used, including a knife or a diagonal cutter. As shown in FIG. 3, slits 56 define a tongue 58. As shown if FIG. 4, a process in accordance with the present embodiment includes the step of positioning tongue 58 at an obtuse angle relative to the longitudinal axis of middle shaft portion 28. In this manner, tongue 58 forms a shelf 60. An inner 62 may be positioned proximate shelf 60 as shown in FIG. 4. A distal end of inner 62 is inserted into a lumen defined by distal shaft portion 30. Proximal portion 52 of distal shaft portion 30 is inserted into the lumen defined by distal portion 50 of middle shaft portion 28.

A first mandrel 66 may be inserted into the lumen of middle shaft portion 28 and the lumen of distal shaft portion 30 as shown in FIG. 6. Also as shown in FIG. 6, a second mandrel 68 may be inserted into guidewire lumen 40 of inner 62. The assembly of FIG. 6 may be inserted into a sleeve 76. Heat and pressure may be applied to transition region 32. In a presently preferred method, the assembly is positioned between a first die and a second die of a compression fixture. The compression fixture may then be closed around the assembly. In this presently preferred method, closing the first die and the second die upon the assembly substantially simultaneously provides for uniform heating of the assembly when the dies are heated. In a presently preferred embodiment, the first die and the second die each include a cavity. Also, in a presently preferred embodiment, the cavity of the first die and the cavity of the second die are adapted to apply pressure to an outer surface of the assembly.

A number of methods may be used to heat transition region 32 including convection, conduction and radiation. For example, compression fixture 70 may include a plurality of electric heaters. These electric heaters would be positioned in intimate contact with compression fixture 70 and would conduct heat to it. Compression fixture 70 would likewise conduct heat to transition region 32. Electric heaters suitable for heating compression fixture 70 are commercially available from Watlow Incorporated of St. Louis, Mo. An example of heating with radiant energy is exposing the regions to be heated to radio frequency energy. An example of heating with convection is placing the compression fixture in a temperature chamber. Temperature chambers suitable for this process are commercially available from Thermotron Corporation of New Holland, Mich. The assembly may be allowed to cool and the assembly may be removed form compression fixture 70.

Assembly 104 may be placed in a rotating fixture. Assembly 104 may be rotated and illuminated with a laser beam. After exposure to laser energy, assembly 104 may be allowed to cool.

The assembly may be submersed in a relatively cool fluid to speed cooling of the assembly. Examples of fluids which may be suitable for some applications include water and air. Relatively cool air may also be impinged onto the assembly. Cold air generators suitable for this purpose are commercially available from ITW Vortec of Cincinnati, Ohio and Exair Corporation of Cincinnati, Ohio. Sleeve 76 may be removed from catheter 20 by grasping ears 82 and applying the force required to tear sleeve 76.

It should be understood that steps may be omitted from this process without deviating from the spirit or scope of the invention. Other methods have been envisioned. Additional exemplary embodiments of the present invention are illustrated in the Figures which follow.

Figure 9:
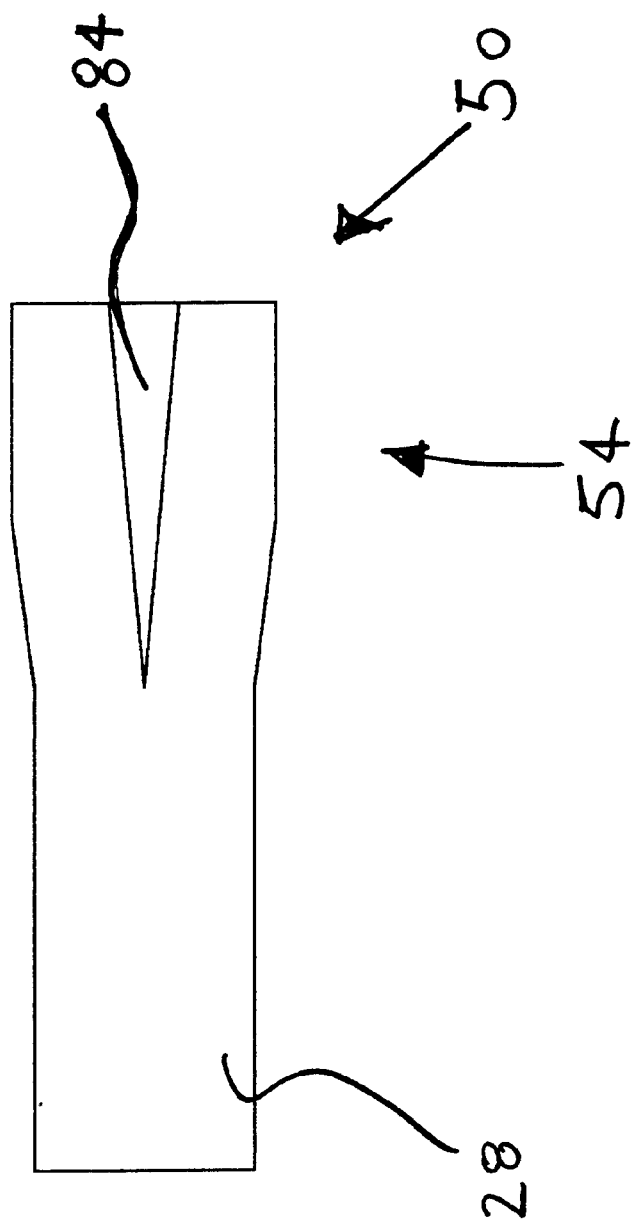
FIG. 9 is a plan view of the distal portion of an generally tubular member in accordance with the an exemplary embodiment of the present invention.

FIG. 9 is a plan view of distal portion 50 of middle shaft portion 28 prior to joining with an additional method in accordance with the present invention. In FIG. 9, middle shaft portion 28 has an enlarged portion 54 proximate its distal portion 50. In a presently preferred embodiment of the present invention, enlarged portion 54 of middle shaft portion 28 facilitates the insertion of proximal portion 52 of distal shaft portion 30 into the lumen defined by distal portion 50 of middle shaft portion 28. The walls of middle shaft portion 28 define a slot 84 disposed proximate the distal end of middle shaft portion 28.

Figure 10:
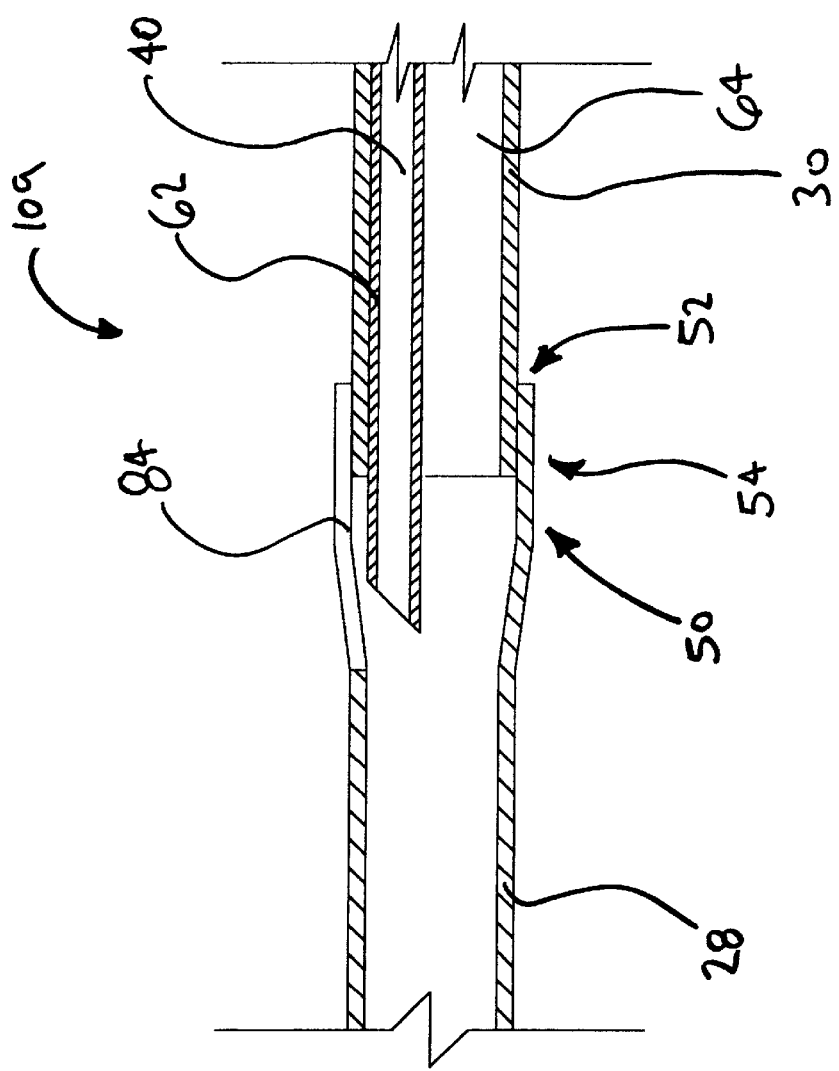
FIG. 10 is a cross sectional view of an assembly in accordance with the present invention, the assembly includes two shaft portions, and an inner tubular member.

FIG. 10 is a cross sectional view of an assembly 109 including middle shaft portion 28. In FIG. 10, the proximal end of distal shaft portion 30 is disposed within the lumen defined by enlarged portion 54 of middle shaft portion 28. An inner tubular member or inner 62 is disposed within the lumens defined by middle shaft portion 28 and distal shaft portion 30, and proximate slot 84 of middle shaft portion 28.

Figure 11:
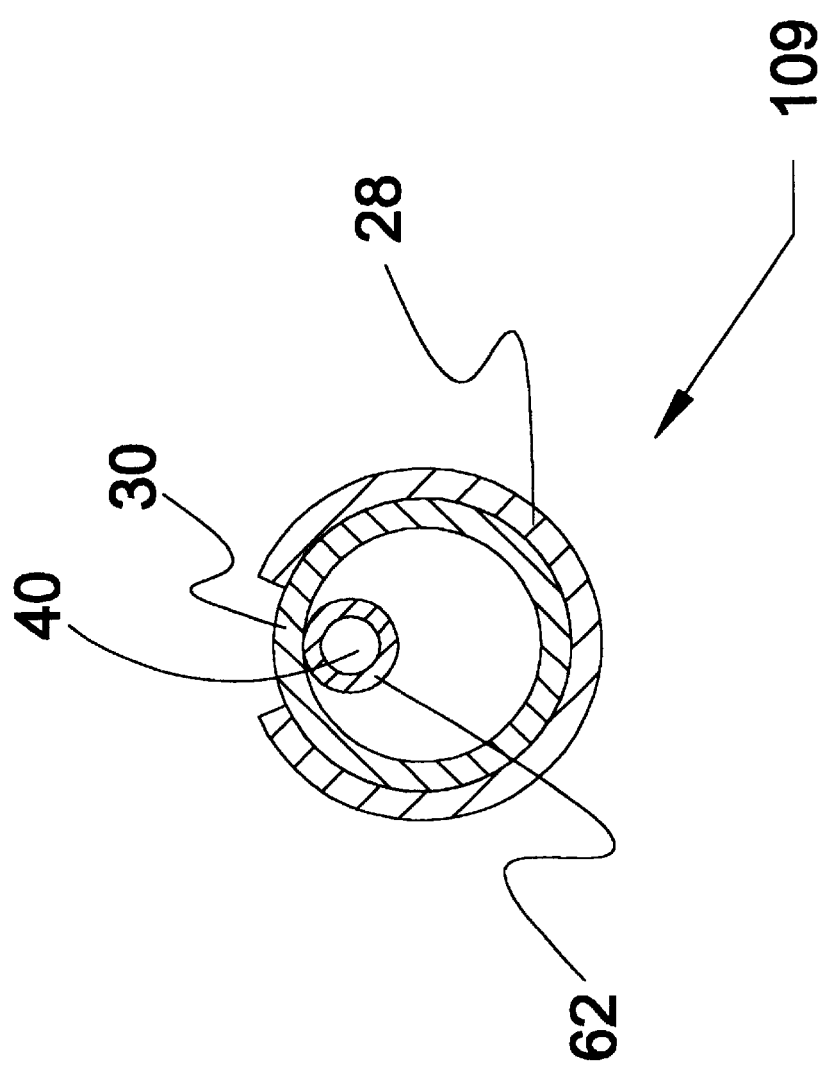
FIG. 11 is a transverse cross sectional view of the assembly of FIG. 10.

FIG. 11 is a transverse cross sectional view of assembly 109 of FIG. 10. In FIG. 11, middle shaft portion 28 is shown disposed about distal shaft portion 30. Inner 62 is shown disposed within the lumens defined by middle shaft portion 28 and distal shaft portion 30. A guide wire lumen 40 defined by inner 62 is also shown in FIG. 11.

A method in accordance with the present invention may be described with reference to FIGS. 8 and 9. The method typically begins with the steps of forming enlarged portion 54 proximate the distal end of middle shaft portion 28 and cutting slot 84 as shown in FIG. 9.

As shown if FIG. 10, a process in accordance with the present invention also includes the step of inserting the distal end of inner 62 into distal lumen 64 defined by distal shaft portion 30. Proximal portion 52 of distal shaft portion 30 is inserted into the lumen defined by distal portion 50 of middle shaft portion 28 and inner 62 is arranged so that it extends through slot 84.

A first mandrel 66 may be inserted into the lumen of middle shaft portion 28 and the lumen of distal shaft portion 30. A second mandrel 68 may be inserted into guidewire lumen 40 of inner 62. The assembly of FIG. 10 may be inserted into a sleeve 76, and positioned in a compression fixture 70. Heat and pressure may the be applied to transition region 32.

Assembly 109 is then removed from compression fixture 70 and transition region 32 is fused. The step of fusing transition region 32 may include the step of illuminating sleeve 76 and transition region 32 with laser light. In a presently preferred method in accordance with the present invention, transition region 32 is rotated while it is illuminated with laser light. After exposure to laser energy, assembly 109 may be allowed to cool. Sleeve 76 may be removed from catheter 20 by tearing or cutting.

Figure 12:
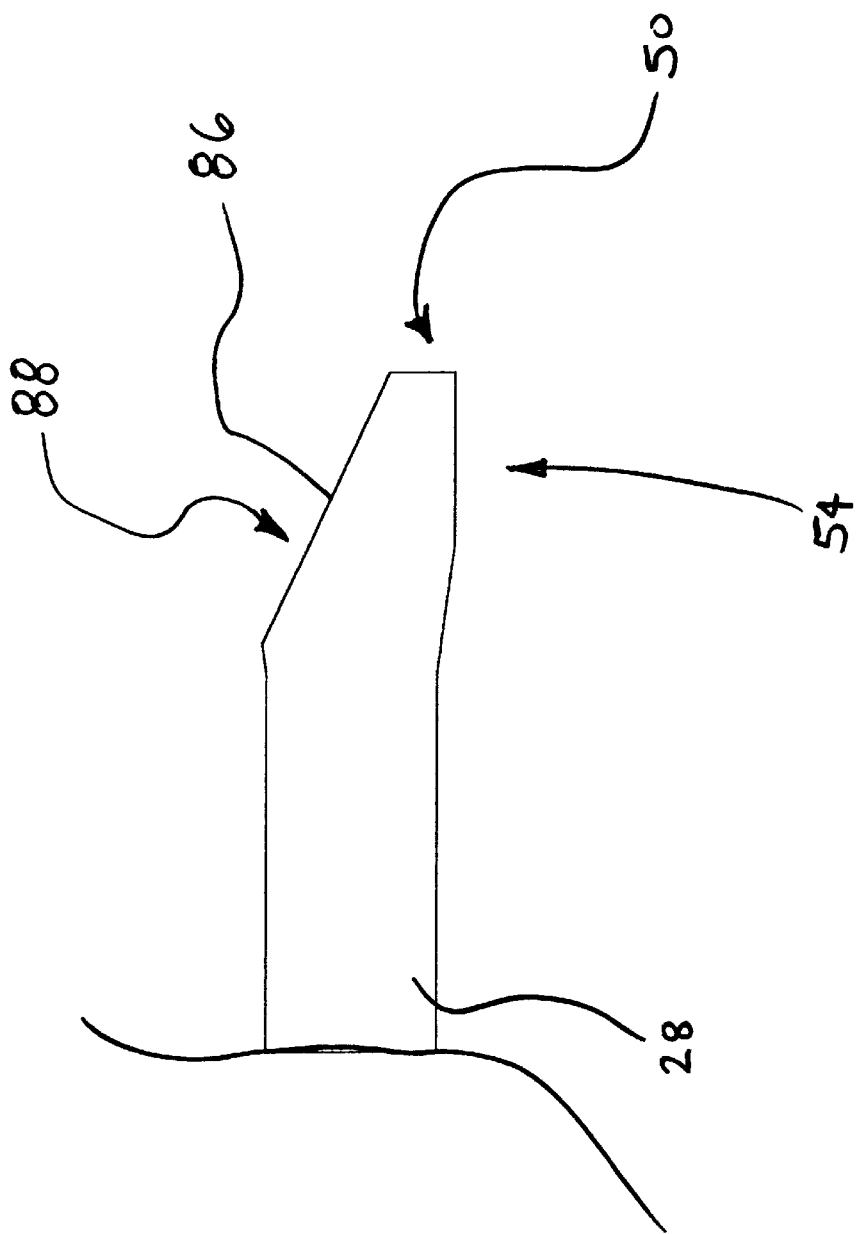
FIG. 12 is a plan view of the distal portion of an generally tubular member in accordance with the an exemplary embodiment of the present invention.

FIG. 12 is a plan view of distal portion 50 of a middle shaft portion 28 in accordance with an additional embodiment in accordance with the present invention. Middle shaft portion 28 includes an enlarged portion 54 proximate its distal portion 50. A bevel 86 has been cut into distal portion 50 of middle shaft portion 28. Bevel 86 defines an opening 88.

Figure 13:
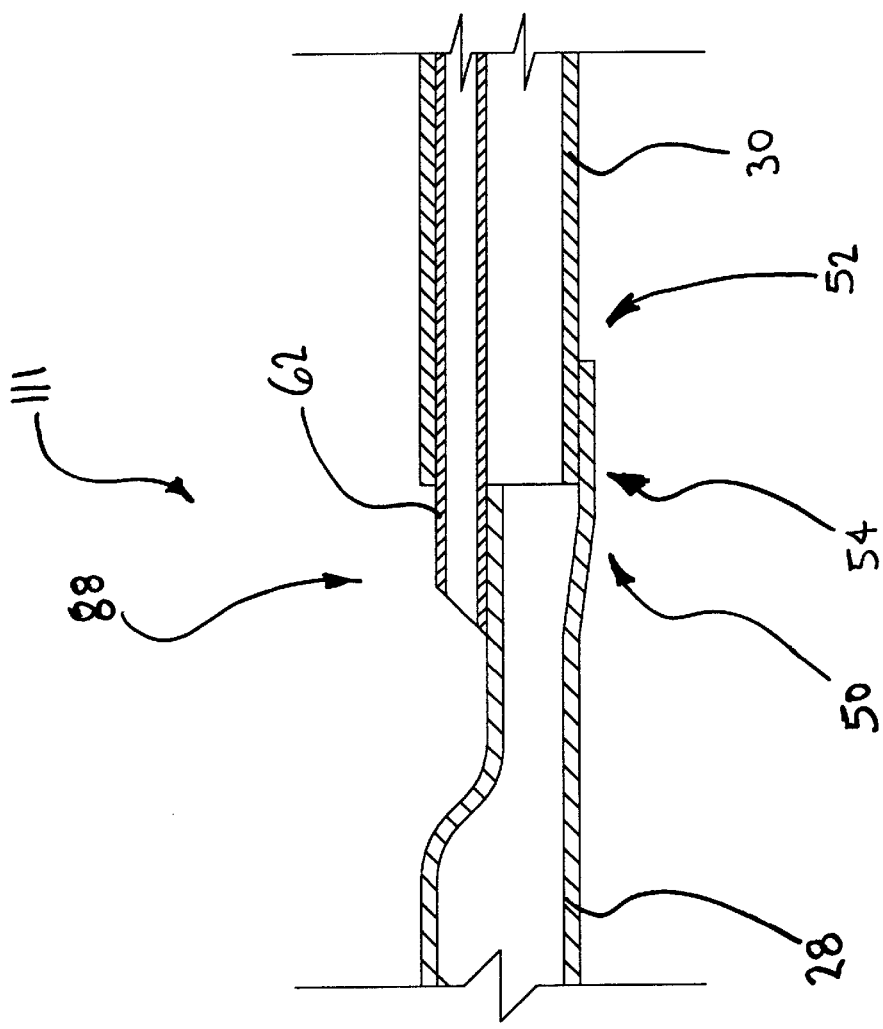
FIG. 13 is a cross sectional view of an assembly in accordance with the present invention, the assembly includes two shaft portions, and an inner tubular member.

FIG. 13 is a cross sectional view of an assembly 111 including middle shaft portion 28 of FIG. 12. In the embodiment of FIG. 13, proximal end 52 of distal shaft portion 30 is disposed proximate enlarged portion 54 of middle shaft portion 28. An inner tubular member or inner 62 is disposed within the lumens defined by middle shaft portion 28 and distal shaft portion 30. Inner 62 extends through opening 88 defined by bevel 86 of middle shaft portion 28. Methods in accordance with the present invention may be used to fuse assembly 111 of FIG. 13 to form transition region 32 of catheter 20.

Figure 14:
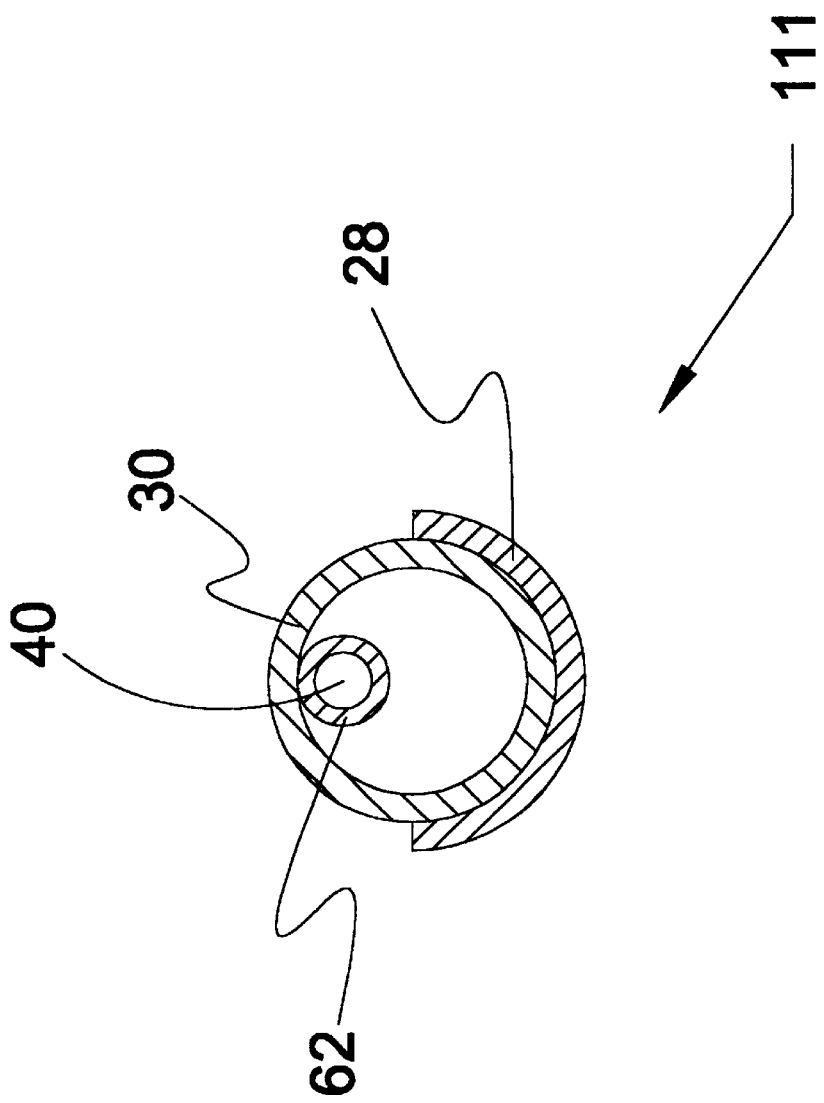
FIG. 14 is a transverse cross sectional view of the assembly of FIG. 13.

FIG. 14 is a transverse cross sectional view of assembly 111 of FIG. 13. In FIG. 14, middle shaft portion 28 is shown disposed about distal shaft portion 30. Inner 62 is shown disposed within the lumens defined by middle shaft portion 28 and distal shaft portion 30. A guide wire lumen 40 defined by inner 62 is also shown in FIG. 14.

Figure 15:
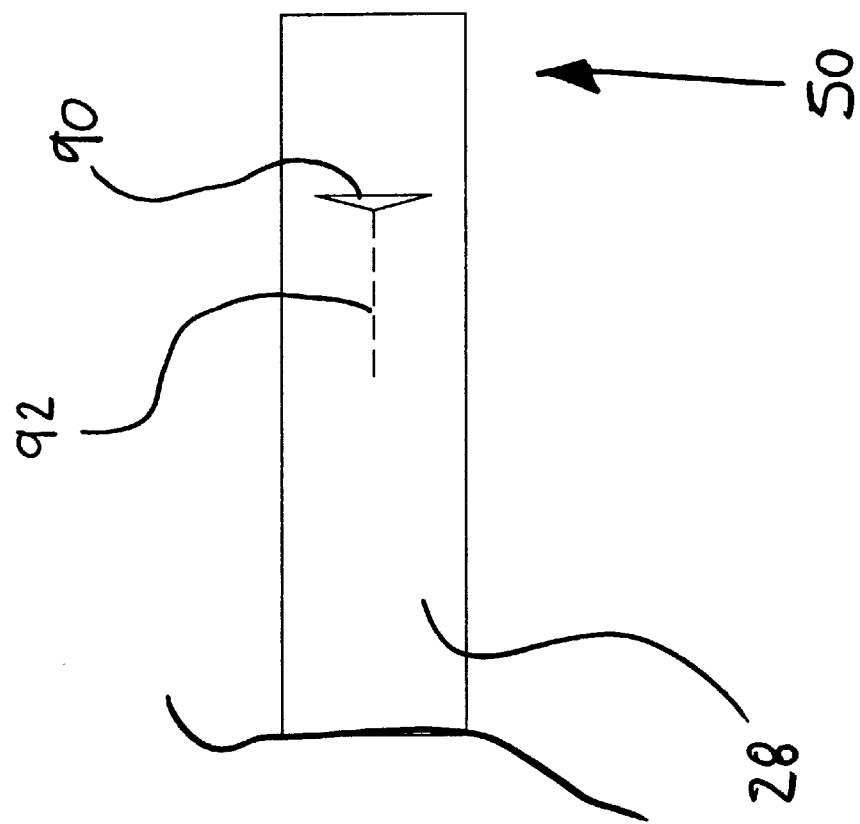
FIG. 15 is a plan view of the distal portion of an generally tubular member in accordance with the an exemplary embodiment of the present invention.

FIG. 15 is a plan view of distal portion 50 of a middle shaft portion 28 in accordance with yet another embodiment in accordance with the present invention. Middle shaft portion 28 defines an aperture 90. A fold 92 is formed by the wall of middle shaft portion 28 proximate aperture 90.

Figure 16:
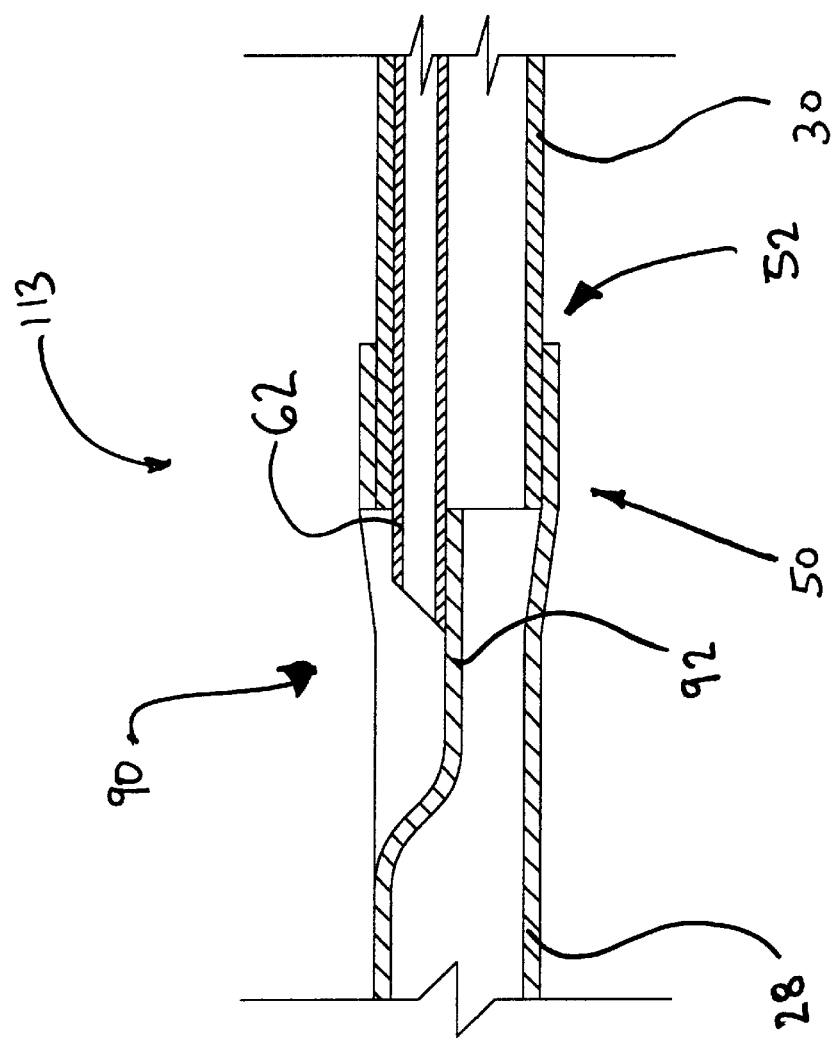
FIG. 16 is a cross sectional view of an assembly in accordance with the present invention, the assembly includes two shaft portions, and an inner tubular member.

FIG. 16 is a cross sectional view of an assembly 113 including middle shaft portion 28 of FIG. 15. In the embodiment of FIG. 16, proximal end 52 of distal shaft portion 30 is disposed within the lumen defined by distal portion 50 of middle shaft portion 28. An inner tubular member or inner 62 is disposed within the lumens defined by middle shaft portion 28 and distal shaft portion 30. Inner 62 extends through aperture 90 and is disposed proximate fold 92. Methods in accordance with the present invention may be used to fuse assembly 113 of FIG. 16 to form transition region 32 of catheter 20.

FIG. 17 is a transverse cross sectional view of assembly 113 of FIG. 16. In FIG. 17, middle shaft portion 28 is shown disposed about distal shaft portion 30. Inner 62 is shown disposed within the lumens defined by middle shaft portion 28 and distal shaft portion 30. A guide wire lumen 40 defined by inner 62 is also shown in FIG. 17.

Figure 19:
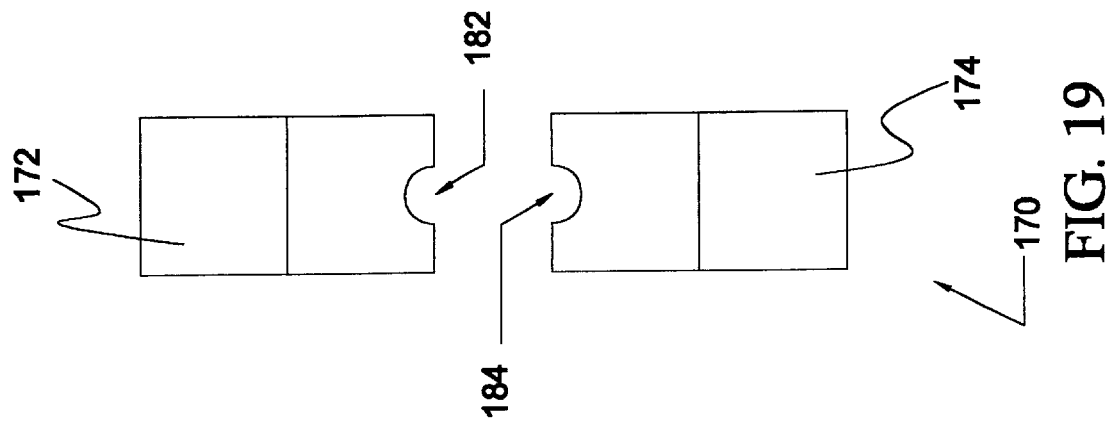
FIG. 19 is a plan view of the compression fixture of FIG. 18.
Figure 18:
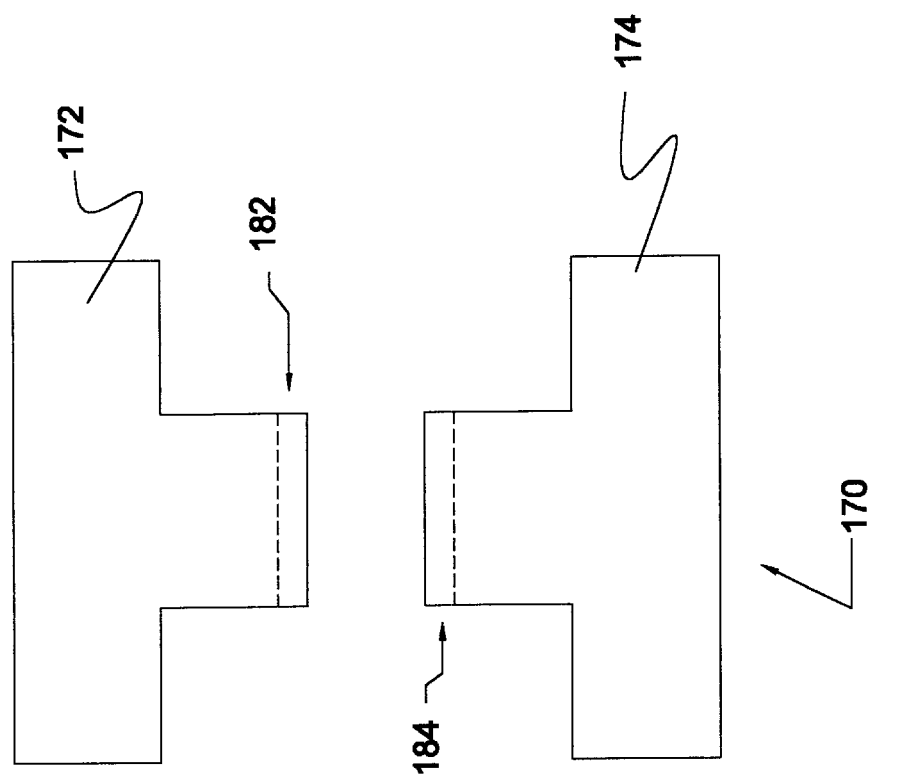
FIG. 18 is a plan view of a compression fixture including a first die having a cavity, and a second die having a cavity.

FIG. 18 is a plan view of a compression fixture 170 including a first die 172 and a second die 174. First die 172 includes a cavity 182. Likewise, second die 174 includes a cavity 184. FIG. 19 is an additional plan view of compression fixture 170 of FIG. 18.

Having thus described the preferred embodiments of the present invention, those of skill in the art will readily appreciate that yet other embodiments may be made and used within the scope of the claims hereto attached.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A method of forming a catheter shaft having a guidewire port, the method comprising the steps of;

providing a first shaft portion having a bonding portion disposed proximate a bonding end thereof, an ancillary end, and a lumen extending therethrough;

providing a second shaft portion having a bonding portion disposed proximate a bonding end thereof, an ancillary end, and a lumen extending therethrough;

providing an inner member having a proximal end, a distal end, and a lumen extending therebetween;

slitting a wall of the first shaft portion to create an opening defined by the wall of the first shaft portion;

inserting the proximal end of the inner member through the opening defined by the wall of the first shaft portion;

inserting the distal end of the inner member into the lumen of the second shaft portion;

inserting the bonding end of the second shaft portion into a lumen defined by bonding portion of the first shaft portion such that the bonding portion of the first shaft portion overlays the bonding portion of the second shaft portion; and bonding the bonding portion of the first shaft portion to the bonding portion of the second shaft portion.

2. The method of claim 1, further including the step of applying heat and pressure to an outer surface of the bonding area of the first shaft portion.

3. The method of claim 1, further including the step of positioning a generally tubular sleeve so that it overlays the bonding area of the first shaft portion.

4. The method of claim 1, further including the steps of positioning a generally tubular sleeve so that it overlays the bonding area of the first shaft portion, and applying heat and pressure to an outer surface of the sleeve.

5. The method of claim 1, further including the step of deforming the bonding end of the first shaft portion to form a flare.

6. The method of claim 1, wherein the first shaft portion includes a support member comprising a plurality of filaments.

7. The method of claim 1, wherein the step of bonding the bonding portion of the first shaft portion to the bonding portion of the second shaft portion includes the step of exposing the bonding portion of the first shaft portion and the bonding portion of the second shaft portion to electromagnetic waves.

8. The method of claim 1, wherein the step of bonding the bonding portion of the first shaft portion to the bonding portion of the second shaft portion includes the step of exposing the bonding portion of the first shaft portion and the bonding portion of the second shaft portion to a hot fluid.

9. The method of claim 1, wherein the step of bonding the bonding portion of the first shaft portion to the bonding portion of the second shaft portion includes the step of heating the bonding portion of the first shaft portion and the bonding portion of the second shaft portion.

10. The method of claim 1, wherein the step of bonding the bonding portion of the first shaft portion to the bonding portion of the second shaft portion includes the step of heating the bonding portion of the first shaft portion and the bonding portion of the second shaft portion with a laser beam.

11. The method of claim 1, wherein the step of bonding the bonding portion of the first shaft portion to the bonding portion of the second shaft portion includes the steps of rotating the first shaft portion and the second shaft portion and directing a laser beam toward the bonding portion of the first shaft portion and the bonding portion of the second shaft portion.

12. The method of claim 1, wherein the step of bonding the bonding portion of the first shaft portion to the bonding portion of the second shaft portion includes the step of exposing the bonding portion of the first shaft portion and the bonding portion of the second shaft portion to hot air.

13. A method of forming a catheter shaft segment having a guidewire port, the method comprising the steps of:
  providing a first shaft portion having a bonding portion disposed proximate a bonding end thereof, an ancillary end, and a lumen extending therethrough;
  the first shaft portion comprising a support member encased in a substrate material, the support member having a plurality of filaments;
  providing a second shaft portion having a bonding portion disposed proximate a bonding end thereof, an ancillary end, and a lumen extending therethrough;
  providing an inner member having a proximal end, a distal end, and a lumen extending therebetween;
  slitting a wall of the first shaft portion to create an opening defined by the wall of the first shaft portion;
  inserting the proximal end of the inner member through the opening defined by the wall of the first shaft portion;
  inserting the distal end of the inner member into the lumen of the second shaft portion;
  inserting the bonding end of the second shaft portion into a lumen defined by the bonding portion of the first shaft portion such that the bonding portion of the first shaft portion overlays the bonding portion of the second shaft portion;
  inserting a first mandrel into the lumen of the first shaft portion;
  inserting a second mandrel into the lumen of the inner member; applying pressure to an outer surface of the bonding portion of the first shaft portion; and heating the bonding portion of the first shaft portion and the bonding portion of the second shaft portion to form a bond therebetween.

14. The method of claim 13, further including the step of positioning a generally tubular sleeve so that it overlays the bonding area of the first shaft portion.

15. The method of claim 13, further including the step of deforming the bonding end of the first shaft portion to form a flare.

16. The method of claim 13, wherein the second shaft portion includes a support member comprising a plurality of filaments.

17. The method of claim 13, wherein the step of heating the bonding portion of the first shaft portion and the bonding portion of the second shaft portion includes the step of exposing the bonding portion of the first shaft portion and the bonding portion of the second shaft portion to electromagnetic waves.

18. The method of claim 13, wherein the step of heating the bonding portion of the first shaft portion and the bonding portion of the second shaft portion includes the step of exposing the bonding portion of the first shaft portion and the bonding portion of the second shaft portion to hot fluid.

19. The method of claim 13, wherein the step of heating the bonding portion of the first shaft portion and the bonding portion of the second shaft portion includes the step of directing a laser beam toward the bonding portion of the first shaft portion and the bonding portion of the second shaft portion.

20. The method of claim 13, wherein the step of heating the bonding portion of the first shaft portion and the bonding portion of the second shaft portion includes the steps of rotating the first shaft portion and the second shaft portion and directing a laser beam toward the bonding portion of the first shaft portion and the bonding portion of the second shaft portion.

21. The method of claim 13, wherein the step of bonding the bonding portion of the first shaft portion to the bonding portion of the second shaft portion includes the step of exposing the bonding portion of the first shaft portion and the bonding portion of the second shaft portion to hot air.

22. A method of forming a catheter shaft segment having a guidewire port, the method comprising the steps of,
  providing a first shaft portion having a bonding portion disposed proximate a bonding end thereof, an ancillary end, and a lumen extending therethrough;
  providing a second shaft portion having a bonding portion disposed proximate a bonding end thereof, an ancillary end, and a lumen extending therethrough; providing an inner member having a proximal end, a distal end, and a lumen extending therebetween;
  deforming the bonding end of the first shaft portion to form a flare;
  slitting a wall of the first shaft portion to create an opening defined by the wall of the first shaft portion;
  inserting the proximal end of the inner member through the opening defined by the wall of the first shaft portion;
  inserting the distal end of the inner member into the lumen of the second shaft portion;
  inserting the bonding end of the second shaft portion into a lumen defined by bonding portion of the first shaft portion such that the bonding portion of the first shaft portion overlays the bonding portion of the second shaft portion;
  inserting a first mandrel into the lumen of the first shaft portion;
  urging the first mandrel further so that a portion thereof is disposed within the lumen of the second shaft portion;
  inserting a second mandrel into the lumen of the inner member;
  positioning a generally tubular sleeve so that it overlays the bonding portion of the first shaft portion;
  applying pressure to an outer surface of the sleeve;
  removing the pressure applied to the outer surface of the sleeve; and
  heating the bonding portion of the first shaft portion and the bonding portion of the second shaft portion to form a bond therebetween.

23. The method of claim 22, wherein the first shaft portion includes a support member comprising a plurality of filaments.

24. The method of claim 22, wherein the step of heating the bonding portion of the first shaft portion and the bonding portion of the second shaft portion includes the step of exposing the bonding portion of the first shaft portion and the bonding portion of the second shaft portion to electromagnetic waves.

25. The method of claim 22, wherein the step of heating the bonding portion of the fist shaft portion and the bonding portion of the second shaft portion includes the step of exposing the bonding portion of the first shaft portion and the bonding portion of the second shaft portion to a hot fluid.

26. The method of claim 23, wherein the step of heating the bonding portion of the first shaft portion and the bonding portion of the second shaft portion includes the step of directing a laser beam toward the bonding portion of the first shaft portion and the bonding portion of the second shaft portion.

27. The method of claim 22, wherein the step of heating the bonding portion of the first shaft portion and the bonding portion of the second shaft portion includes the steps of rotating the first shaft portion and the second shaft portion and directing a laser beam toward the bonding portion of the first shaft portion and the bonding portion of the second shaft portion.

28. The method of claim 22, wherein the step of bonding the bonding portion of the first shaft portion to the bonding portion of the second shaft portion includes the step of exposing the bonding portion of the first shaft portion and the bonding portion of the second shaft portion to hot air.

* * * * *